(12) United States Patent
Jones et al.

(10) Patent No.: US 9,321,987 B2
(45) Date of Patent: Apr. 26, 2016

(54) ENCAPSULATED BENEFIT AGENTS

(71) Applicant: Conopco,Inc., Englewood Cliffs, NJ (US)

(72) Inventors: Craig Warren Jones, Merseyside (GB); Changxi Li, Shanghai (CN); Xiaoyun Pan, Shanghai (CN); Yuanyuan Zhang, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/443,109

(22) PCT Filed: Nov. 5, 2013

(86) PCT No.: PCT/EP2013/073073
§ 371 (c)(1),
(2) Date: May 15, 2015

(87) PCT Pub. No.: WO2014/075956
PCT Pub. Date: May 22, 2014

(65) Prior Publication Data
US 2015/0291919 A1   Oct. 15, 2015

(30) Foreign Application Priority Data

Nov. 19, 2012   (WO) ................ PCT/CN2012/084834

(51) Int. Cl.
| | |
|---|---|
| C11D 3/50 | (2006.01) |
| A61Q 5/02 | (2006.01) |
| C11B 9/00 | (2006.01) |
| A61Q 5/12 | (2006.01) |
| A61Q 15/00 | (2006.01) |
| A61K 8/11 | (2006.01) |
| C11D 3/37 | (2006.01) |
| C11D 17/00 | (2006.01) |
| A61Q 19/10 | (2006.01) |

(52) U.S. Cl.
CPC . *C11D 3/505* (2013.01); *A61K 8/11* (2013.01); *A61Q 5/02* (2013.01); *A61Q 5/12* (2013.01); *A61Q 15/00* (2013.01); *A61Q 19/10* (2013.01); *C11B 9/0015* (2013.01); *C11B 9/0034* (2013.01); *C11B 9/0061* (2013.01); *C11D 3/3753* (2013.01); *C11D 17/0039* (2013.01); *A61K 2800/56* (2013.01)

(58) Field of Classification Search
CPC .................................................. A61K 2800/56
See application file for complete search history.

(56) References Cited

U.S. PATENT DOCUMENTS

| 7,833,960 B2 | 11/2010 | Lei | |
|---|---|---|---|
| 2007/0048337 A1 * | 3/2007 | Arthur ..................... | A61K 9/06 424/400 |

FOREIGN PATENT DOCUMENTS

| CN | 101254448 | 9/2008 |
|---|---|---|
| EP | 1275378 | 1/2003 |
| WO | WO2005121186 | 12/2005 |
| WO | WO2005121886 A1 | 12/2005 |
| WO | WO2009103576 | 8/2009 |
| WO | WO2010015493 A1 | 2/2010 |
| WO | WO2012007438 | 1/2012 |

OTHER PUBLICATIONS

Gebben, B, Van Den Berg HWA, Bargeman D, Smolders CA, Polymer, Intramolecular crosslinking of poly (vinyl alcohol), Oct. 1, 1985, pp. 1737-1740, vol. 26.
Search Report in PCT/EP201307307, Nov. 2, 2014.
Search Report in PCTCN2012084834, Aug. 29, 2013.
Written Opinion in PCTCN2012084834, Aug. 29, 2013.
Written Opinion in PCTEP2013073073, Nov. 2, 2014.

* cited by examiner

*Primary Examiner* — Adam C Milligan
*Assistant Examiner* — Sarah Alawadi
(74) *Attorney, Agent, or Firm* — Greenberg Traurig, LLP

(57) ABSTRACT

The invention provides improved deposition and reduced leakage benefits from a particle comprising: (a) a core comprising a benefit agent; (b) a shell, wherein the shell comprises a crosslinked, hydrophobically modified polyvinyl alcohol, which comprises a crosslinking agent comprising i) a first dextran aldehyde having a molecular weight of from 2,000 to 50,000 Da; and ii) a second dextran aldehyde having a molecular weight of from greater than 50,000 to 2,000,000 Da.

15 Claims, No Drawings

ENCAPSULATED BENEFIT AGENTS

TECHNICAL FIELD

The present invention is concerned with the delivery of particles comprising benefit agents, to substrates, with processes for the manufacture of said particles and the manufacture and use of formulations comprising said particles. It will be specifically described herein with reference to laundry treatment compositions but has other and broader applications.

BACKGROUND

Many home care and personal care formulations seek to deliver benefit agents to substrates such as textiles, hard surfaces, hair and skin. Encapsulation of the benefit agent in particles has been proposed as a means of enhancing delivery. Encapsulation of perfumes has generated particular interest and activity in recent years.

However, there is still much room for improvement as consumer preference for improved fragrance perception at multiple stages of the wash process, such as at the end of the wash, and for ever longer lasting perfume performance, drives commercial interest in this area.

Leakage of encapsulates remains a problem which not only causes reduced performance but also restricts the ingredients that can be stably encapsulated.

Melamine formaldehyde capsules are known but, disadvantageously, need to be used in conjunction with a formaldehyde scavenger.

US 2008 146478 (International Flavors and Fragrances Inc) discloses a microcapsule comprising an active material, a nanoscaled material and an encapsulating polymer. The encapsulating polymer is selected from the group consisting of a vinyl polymer, an acrylate polymer, an acrylate acrylamide copolymer, melamine-formaldehyde polymer, urea-formaldehyde polymer and mixtures thereof to form a polymer encapsulated fragrance. See claims 1, 2 and sections [0111] and [0113].

US 2004 071742 (International Flavors and Fragrances Inc) discloses a composition comprising: a fragrance material; said fragrance material encapsulated by a polymer to provide a polymer encapsulated fragrance; the polymer encapsulated fragrance is further coated by a cationic polymer.

US 2004 072719 (International Flavors and Fragrances Inc) discloses a composition comprising: a fragrance material; said fragrance material encapsulated by a polymer to provide a polymer encapsulated fragrance; the polymer encapsulated fragrance is further coated by a polyamine polymer.

U.S. Pat. No. 5,460,817 (Allied Colloids Ltd) discloses a particulate composition comprising particles having an anhydrous core comprising (a) a solid matrix polymer and an active ingredient distributed throughout the solid matrix polymer and (b) an outer protective coacervated polymer shell. The outer shell is formed of a cross-linked polymer (Polyvinyl alcohol).

WO 92/06672 (Revlon Inc.) discloses a microencapsulate comprising one or more antiperspirant salts encapsulated within a shell wall which is susceptible to osmotic, enzymatic, or electrolytic degradation, or degradation due to water solubility of the shell wall.

We have now surprisingly found that the use of crosslinking agent comprising a mixture of dextrans having different molecular weights, and the cross-linked mPVOH capsules thus produced, leads to marked improvement in deposition efficiency and a corresponding consumer perceivable increase in benefit delivery.

Advantageously, the new capsules are made substantially from renewable feedstocks, which helps to reduce environmental impact.

BRIEF DESCRIPTION OF THE INVENTION

Accordingly, in a first aspect the present invention provides a particle comprising:
(a) a core comprising a benefit agent;
(b) a shell, wherein the shell comprises a crosslinked, hydrophobically modified polyvinyl alcohol, which comprises a crosslinking agent comprising
  i) a first dextran aldehyde having a molecular weight of from 2,000 to 50,000 Da; and
  ii) a second dextran aldehyde having a molecular weight of from greater than 50,000 to 2,000,000 Da.

A second aspect of the present invention provides a home care or personal care composition comprising at least one particle according to the first aspect of the invention, the composition preferably being a laundry detergent, laundry conditioner, deodorant, antiperspirant, shampoo, hair conditioner or skin care or skin cleansing product.

A third aspect of the present invention provides a method of treatment of a substrate, preferably wherein the substrate is selected from skin, hair and/or textile material, which includes the step of treating the substrate with a composition comprising particles according to the first aspect of the invention.

DETAILED DESCRIPTION OF THE INVENTION

In order that the present invention may be further and better understood it will be further described below with reference to specific embodiments of the invention and further preferred and/or optional features. All amounts quoted are wt % of the total composition unless otherwise stated.

The Particle

The core is typically formed in an inner region of the particle and provides a sink for the benefit agent. The "shell" protects the benefit agent and regulates the flow of benefit agent into and out of the core.

Particle Size

The person of ordinary skill in the art will know how to measure the particle size distribution of the capsules, for example, by utilising a Malvern Mastersizer 2000. Typically, the particle has an average diameter of less than 5-50 micron, preferably from 10 to 40 micron, more preferably from 25 to 35 and most preferably 30 micron.

The Core

The core comprises one or more benefit agent.

Advantageously the benefit agent is a hydrophobic benefit agent, preferably an organoleptic benefit agent, for example a flavour or fragrance (the terms "fragrance" and "perfume" are used interchangeably herein).

Benefit Agents

Various benefit agents can be incorporated into the particles. Where the end use of the particles is in connection with a surfactant-containing system, any compatible benefit agent which can provide a benefit to a substrate which is treated with a surfactant composition can be used. Preferred benefit agents are in the laundry field, for example fabric benefit agents, and benefit agents which provide a benefit to a laundry wash and/or rinse medium. In the alternative benefit agents may provide a skin or hair related benefit. Advantages of the particles of the invention in the presence of surfactant are a good retention of the benefit agent on storage of a formulation and controllable release of the benefit agent during and after product usage.

Preferred examples include flavours, fragrances, enzymes, antifoams, fluorescer, shading dyes and/or pigments, conditioning agents (for example water-insoluble quaternary ammonium materials and/or silicones), sunscreens, ceramides, antioxidants, reducing agents, sequestrants, colour care additives, density matching polymers, photo-bleaches, lubricants, unsaturated oils, emollients/moisturiser and antimicrobial agents, most preferred are fragrances and antimicrobial agents.

Preferred antimicrobials include Triclosan™, climbazole, octapyrox, ketoconizole, zinc pyrithione, and quaternary ammonium compounds.

Preferred sunscreens and/or skin lightening agents are vitamin B3 compounds. Suitable vitamin B3 compounds are selected from niacin, niacinamide, nicotinyl alcohol, or derivatives or salts thereof. Other vitamins which act as skin lightening agents can be advantageously included in the skin lightening composition to provide for additional skin lightening effects. These include vitamin B6, vitamin C, vitamin A or their precursors. Mixtures of the vitamins can also be employed in the composition of the invention. An especially preferred additional vitamin is vitamin B6. Other non-limiting examples of skin lightening agents useful herein include adapalene, aloe extract, ammonium lactate, arbutin, azelaic acid, butyl hydroxy anisole, butyl hydroxy toluene, citrate esters, deoxyarbutin, 1,3 diphenyl propane derivatives, 2,5 dihydroxyl benzoic acid and its derivatives, 2-(4-acetoxyphenyl)-1,3 dithane, 2-(4-Hydroxylphenyl)-1,3 dithane, ellagic acid, gluco pyranosyl-1-ascorbate, gluconic acid, glycolic acid, green tea extract, 4-Hydroxy-5-methyl-3[2H]-furanone, hydroquinone, 4 hydroxyanisole and its derivatives, 4-hydroxy benzoic acid derivatives, hydroxycaprylic acid, inositol ascorbate, kojic acid, lactic acid, lemon extract, linoleic acid, magnesium ascorbyl phosphate, 5-octanoyl salicylic acid, 2,4 resorcinol derivatives, 3,5 resorcinol derivatives, salicylic acid, 3,4,5 trihydroxybenzyl derivatives, and mixtures thereof. Preferred sunscreens useful in the present invention are 2-ethylhexyl-p-methoxycinnamate, butyl methoxy dibenzoylmethane, 2-hydroxy-4-methoxybenzophenone, octyl dimethyl-p-aminobenzoic acid and mixtures thereof. Particularly preferred sunscreen is chosen from 2-ethyl hexyl-p-methoxycinnamate, 4-t-butyl-4'-methoxydibenzoyl-methane or mixtures thereof. Other conventional sunscreen agents that are suitable for use in the skin lightening composition of the invention include 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl)) aminobenzoate, 2-ethylhexyl-2-cyano-3,3-diphenylacrylate, 2-ethylhexylsalicylate, glyceryl-p-aminobenzoate, 3,3,5-trimethylcyclohexyl-salicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonic benzoxazoic acid and mixtures of these compounds.

Preferred anti-oxidants include vitamin E, retinol, antioxiants based on hydroxytoluene such as Irganox™ or commercially available antioxidants such as the Trollox™ series.

Perfume and fragrance materials (which include pro-fragrances) are a particularly preferred benefit agent.

The pro-fragrance can, for example, be a food lipid. Food lipids typically contain structural units with pronounced hydrophobicity. The majority of lipids are derived from fatty acids. In these 'acyl' lipids the fatty acids are predominantly present as esters and include mono-, di-, triacyl glycerols, phospholipids, glycolipids, diol lipids, waxes, sterol esters and tocopherols. In their natural state, plant lipids comprise antioxidants to prevent their oxidation. While these may be at least in part removed during the isolation of oils from plants some antioxidants may remain. These antioxidants can be pro-fragrances. In particular, the carotenoids and related compounds including vitamin A, retinol, retinal, retinoic acid and provitamin A are capable of being converted into fragrant species including the ionones, damascones and damscenones. Preferred pro-fragrance food lipids include olive oil, palm oil, canola oil, squalene, sunflower seed oil, wheat germ oil, almond oil, coconut oil, grape seed oil, rapeseed oil, castor oil, corn oil, cottonseed oil, safflower oil, groundnut oil, poppy seed oil, palm kernel oil, rice bran oil, sesame oil, soybean oil, pumpkin seed oil, jojoba oil and mustard seed oil. Perfume components which are odiferous materials are described in further detail below.

The perfume is typically present in an amount of from 10-85% by total weight of the particle, preferably from 15 to 75% by total weight of the particle. The perfume suitably has a molecular weight of from 50 to 500 Dalton. Pro-fragrances can be of higher molecular weight, being typically 1-10 kD.

Useful components of the perfume include materials of both natural and synthetic origin. They include single compounds and mixtures. Specific examples of such components may be found in the current literature, e.g., in Fenaroli's Handbook of Flavour Ingredients, 1975, CRC Press; Synthetic Food Adjuncts, 1947 by M. B. Jacobs, edited by Van Nostrand; or Perfume and Flavour Chemicals by S. Arctander 1969, Montclair, N.J. (USA). These substances are well known to the person skilled in the art of perfuming, flavouring, and/or aromatizing consumer products, i.e., of imparting an odour and/or a flavour or taste to a consumer product traditionally perfumed or flavoured, or of modifying the odour and/or taste of said consumer product.

By perfume in this context is not only meant a fully formulated product fragrance, but also selected components of that fragrance, particularly those which are prone to loss, such as the so-called 'top notes'.

Top notes are defined by Poucher (Journal of the Society of Cosmetic Chemists 6(2):80 [1955]). Examples of well known top-notes include citrus oils, linalool, linalyl acetate, lavender, dihydromyrcenol, rose oxide and cis-3-hexanol. Top notes typically comprise 15-25% wt of a perfume composition and in those embodiments of the invention which contain an increased level of top-notes it is envisaged at that least 20% wt would be present within the particle.

Typical perfume components which it is advantageous to employ in the embodiments of the present invention include those with a relatively low boiling point, preferably those with a boiling point of less than 300, preferably 100-250 Celsius.

It is also advantageous to encapsulate perfume components which have a low LogP (i.e. those which will be partitioned into water), preferably with a LogP of less than 3.0. These materials, of relatively low boiling point and relatively low Log P have been called the "delayed blooming" perfume ingredients and include the following materials:

Allyl Caproate, Amyl Acetate, Amyl Propionate, Anisic Aldehyde, Anisole, Benzaldehyde, Benzyl Acetate, Benzyl Acetone, Benzyl Alcohol, Benzyl Formate, Benzyl Iso Valerate, Benzyl Propionate, Beta Gamma Hexenol, Camphor Gum, Laevo-Carvone, d-Carvone, Cinnamic Alcohol, Cinamyl Formate, Cis-Jasmone, cis-3-Hexenyl Acetate, Cuminic Alcohol, Cyclal C, Dimethyl Benzyl Carbinol, Dimethyl Benzyl Carbinol Acetate, Ethyl Acetate, Ethyl Aceto Acetate, Ethyl Amyl Ketone, Ethyl Benzoate, Ethyl Butyrate, Ethyl Hexyl Ketone, Ethyl Phenyl Acetate, Eucalyptol, Eugenol, Fenchyl Acetate, Flor Acetate (tricyclo Decenyl Acetate), Frutene (tricyclco Decenyl Propionate), Geraniol, Hexenol, Hexenyl Acetate, Hexyl Acetate, Hexyl Formate, Hydratropic Alcohol, Hydroxycitronellal, Indone, Isoamyl Alcohol, Iso Menthone, Isopulegyl Acetate, Isoquinolone, Ligustral, Linalool, Linalool Oxide, Linalyl Formate, Menthone, Menthyl Acetphenone, Methyl Amyl Ketone, Methyl Anthranilate, Methyl Benzoate, Methyl Benyl Acetate, Methyl Eugenol, Methyl Heptenone, Methyl Heptine Carbonate, Methyl Heptyl Ketone, Methyl Hexyl Ketone, Methyl Phenyl Carbinyl Acetate, Methyl Salicylate, Methyl-N-Methyl Anthranilate, Nerol, Octalactone, Octyl Alcohol, p-Cresol, p-Cresol Methyl Ether, p-Methoxy Acetophenone, p-Methyl Acetophenone, Phenoxy Ethanol, Phenyl Acetaldehyde, Phenyl Ethyl Acetate, Phenyl Ethyl Alcohol, Phenyl Ethyl Dimethyl Carbinol, Prenyl Acetate, Propyl Bornate, Pulegone, Rose Oxide, Safrole, 4-Terpinenol, Alpha-Terpinenol, and/or Viridine.

It is commonplace for a plurality of perfume components to be present in a formulation. In the encapsulates of the present invention it is envisaged that there may be four or more, preferably five or more, more preferably six or more or even seven or more different perfume components from the list given of delayed blooming perfumes given above present in the particles.

Another group of perfumes with which the present invention can be applied are the so-called 'aromatherapy' materials. These include many components also used in perfumery, including components of essential oils such as Clary Sage, *Eucalyptus*, Geranium, Lavender, Mace Extract, Neroli, Nutmeg, Spearmint, Sweet Violet Leaf and Valerian. By means of the present invention these materials can be transferred to textile articles that will be worn or otherwise come into contact with the human body (such as handkerchiefs and bed linen).

The core preferably further comprises additional components such as polymeric agents, solvents and mixtures thereof.

Suitable solvents include white mineral oils, natural fatty esters and synthetic fatty esters. Preferred solvents are diethyl phthalate, isopropyl myristate, PEG-400 to PEG 2000 materials, C12-15 alkyl benzoate and mixtures thereof, more preferably isopropyl myristate, PEG-600, C12-15 alkyl benzoate and mixtures thereof.

Suitable polymeric agents include hydrophobically modified polysacharride materials, for example, alkyl derivatised celluloses. Preferred materials are hydroxypropyl cellulose, hydroxyethyl cellulose, hyroxyethylmethyl cellulose, hydroxypropylmethyl cellulose, hydroxybutyl cellulose, hydroxybutyl ethyl cellulose, methyl cellulose and mixtures thereof. Particularly preferred polymeric agents are hydroxypropyl methyl cellulose, methyl cellulose and mixtures thereof.

The polymeric agent is preferably miscible/soluble with the benefit agent. The solvent may be additionally used in order to improve the miscibility/solubility of the polymer.

The Shell

The Dextran

The shell comprises a i) a first dextran aldehyde having a molecular weight of from 2,000 to 50,000 Da, preferably from 5,000 to 30,000 Da, even more preferably from 10,000 to 25,000 Da, still more preferably from 15,000 to 22,000, most preferably 20,000 Da; and ii) a second dextran aldehyde having a molecular weight of from greater than 50,000, to 2,000,000 Da, preferably from 75,000 to 1,000,000, even more preferably from 100,000 to 500,000 Da, still more preferably from 150,000 to 300,000, most preferably 200,000 Da.

Dextran is an α-D-1,6-glucose-linked glucan with sidechains 1-3 linked to the backbone units of the dextran. Typically the degree of branching is approximately 5%. The branches are mostly 1 to 2 glucose units long. It is surprising that an alpha 1-6 polysaccharide should show any affinity for both cellulose and polyester.

The dextran aldehyde materials must contain 2 or more aldehyde groups in order to crosslink.

Amount of Dextran

We have found that the total amount of dextran crosslinker used has an influence on the quality of the capsule. Capsules were suitably uniform and regular when dextran aldehyde was used in an amount of from 2.0 to 5.0 wt %, preferably 2.8 to 3.0 wt %.

The total amount of dextran aldehyde materials (i.e. of high and low molecular weight dextran aldehydes) is preferably from 0.5 to 5.0 wt %, more preferably from 1.0 to 3.5 wt %, most preferably 2.0 to 3.0 wt %, by total weight of the particle.

Ratio of the Two Molecular Weight Dextrans

We have found that the ratio of the second dextran aldehyde (high MWt) to the first dextran aldehyde (low MWt) is important for the quality of the crosslinked mPVOH capsule. The wt/wt ratio of high to low MWt dextran aldehyde is suitably in the range of from 0.1 to 10, preferably from 0.5 to 5 and most preferably from 1 to 2.

The mPVOH

The amount of mPVOH was found to influence the capsule preparation. Uniform and regular capsules could only be obtained in appropriate mPVOH concentration.

Suitable amounts of mPVOH are in the range of from 2 to 50 wt %, preferably from 10 to 30 wt %, most preferably from 18 to 20 wt %.

Below this amount, the perfume droplet was not fully emulsified. At amounts greater than this, the resultant capsules became aggregated due to higher probability of inter-crosslinking between capsules.

PVOH (parent material), which has a degree of hydrolysis of from 60 to 99%, is first reacted with a derivatising material such as butyraldehyde to give the mPVOH.

The mPVOH comprises an alkyl chain, generally between $C_3$ to $C_{18}$. Hydrocarbyl chain lengths greater than 22 are undesirable as the parent material from which the derivatising group is obtained reacts poorly or not at all with the polymeric backbone.

The hydrocarbyl chain length of the original function on the parent material from which the derivatising group is obtained is preferably from 4 to 22, more preferably from 5 to 20.

In this context, the number of carbons in the hydrocarbyl group includes any carbon within the chain attached to any other functional group within the derivatising material. For instance, butyraldehyde has a hydrocarbyl chain length of 4.

The derivatising material is preferably present in the polymer at a level of from 0.1 to 40% by weight, based on the total weight of the polymer, more preferably 2 to 30%, most preferably 5 to 15%, e.g. 8 to 12%.

Where the polymeric backbone is based on PVOH, the derivatising material is preferably present at a level such that the number ratio of the derivative groups to the free hydroxyl pairs on the backbone is from 1:3 to 1:30, more preferably 1:4 to 1:20, most preferably 1:7 to 1:15, e. g. 1:8 to 1:13.

Polyvinyl alcohol based polymers preferred for use herein have an average molecular weight of from 1,000 to 300,000, preferably from 2,000 to 100,000, most preferably from 2,000 to 75,000. Hydrolysis, or alcoholysis, is defined as the percent completion of the reaction where acetate groups on the resin are substituted with hydroxyl, —OH, groups. A hydrolysis range of from 60-99% of PVOH-based film-forming resin is preferred, while a more preferred range of hydrolysis is from about 88-99%. As used in this application, the term "PVOH" includes polyvinyl acetate compounds with levels of hydrolysis disclosed herein.

Preferred PVOH polymers preferably have an average degree of saponification within the range from 70 to 99%, and a viscosity as a 7% solution within the range 100 to 5000 mPa·s at ambient temperature measured at a shear rate of 20 s$^{-1}$.

All of the above polymers include the aforementioned polymer classes whether as single polymers or as copolymers formed of monomer units or as copolymers formed of monomer units derived from the specified class or as copolymers wherein those monomer units are copolymerised with one or more comonomer units.

A particularly preferred polymer for use in the present invention is represented by the formula:

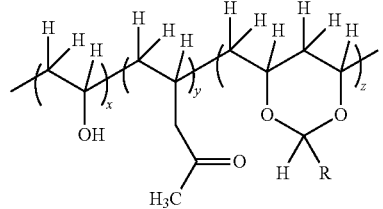

wherein the average number ratio of z to x is within the range of from 1:200 to 1:6, more preferably from 1:100 to 1:8, most preferably from 1:50 to 1:12, e.g. 1:30 to 1:14, y is the residual acetate remaining from the hydrolysis of the parent compound, which is preferably in the range of from 1-20%, more preferably 1-10%, most preferably 1-5% and R is an alkyl or alkenyl group having from 3 to 22 carbon atoms.

More preferably R is an alkyl group having from 3 to 6 carbon atoms. Most preferably R is $C_3H_7$.

Preparation of mPVOH

A 10 wt % solution of PVOH in water was prepared by placing 100 g PVOH (Mowiol 20-98 (trade name), ex Kuraray Specialities) and 900 g demineralised water into a flask and heating to 70° C. To this, 10 ml of hydrochloric acid (36% aqueous solution) was added to catalyse the reaction and then butyraldehyde was added. The mixture was then stirred at 70 C for 5 hours under an inert atmosphere, after which time the heating was stopped and agitation continued for a further 20 hours at room temperature. The reaction mixture was then brought to a pH of 7 using a sodium hydroxide solution.

The resulting solution was precipitated into acetone to yield the acetalised PVOH polymer and washed repeatedly with acetone (500 ml) and then water (50 ml). It was then dried under vacuum at 70 C overnight to yield a white polymer.

Deposition Aids

The particle may comprise a deposition aid. Preferred deposition aids are substantive to proteinaceous, cellulosic, polyester, lipid or polyamide surfaces. By use of such a deposition aid, the efficiency of delivery to a specific substrate may be enhanced.

Deposition aids modify the properties of the exterior of the particle. One particular benefit which can be obtained with these materials is to make the particle more substantive to a desired substrate. Desired substrates include cellulosics (including cotton), polyesters (including those employed in the manufacture of polyester fabrics) and protein-containing substrates (such as skin and hair). Deposition aids are preferably selected from non-hydrolysable substrate-substantive polymers, hydrolysable substrate-substantive polymers and polyester-substantive polymers.

Preferred polysaccharide polymers, whether hydrolysable or not may be derived from a broad range of polysaccharides. Preferably, the polysaccharide is selected from the group consisting of: tamarind gum (preferably consisting of xyloglucan polymers), guar gum, locust bean gum (preferably consisting of galactomannan polymers), and other industrial gums and polymers, which include, but are not limited to, Tara, Fenugreek, Aloe, Chia, Flaxseed, *Psyllium* seed, quince seed, xanthan, gellan, welan, rhamsan, dextran, curdlan, pullulan, scleroglucan, schizophyllan, chitin, hydroxyalkyl cellulose, arabinan (preferably from sugar beets), de-branched arabinan (preferably from sugar beets), arabinoxylan (preferably from rye and wheat flour), galactan (preferably from lupin and potatoes), pectic galactan (preferably from potatoes), galactomannan (preferably from carob, and including both low and high viscosities), glucomannan, lichenan (preferably from icelandic moss), mannan (preferably from ivory nuts), pachyman, rhamnogalacturonan, *acacia* gum, agar, alginates, carrageenan, chitosan, clavan, hyaluronic acid, heparin, inulin, cellodextrins, cellulose, cellulose derivatives and mixtures thereof.

Preferred non-hydrolysable substrate-substantive deposition aids include non-hydrolysable polysaccharides. The polysaccharide preferred for cotton substantivity for example has a β-1,4-linked backbone.

Preferably the polysaccharide is a cellulose, a cellulose derivative, or another β-1,4-linked polysaccharide having an affinity for cellulose, such as polymannan, polyglucan, polyglucomannan, polyxyloglucan and polygalactomannan or a mixture thereof. More preferably, the polysaccharide is selected from the group consisting of polyxyloglucan and polygalactomannan. Most preferably, the deposition aid is locust bean gum, xyloglucan, guar gum or mixtures thereof.

Preferred hydrolysable substrate-substantive deposition aids include hydrolysable polysaccharides. These comprise a polysaccharide which has been modified to render it more water soluble by means of a group covalently attached to the polysaccharide by means of hydrolysable bond. Preferred groups may for example be independently selected from one or more of acetate, propanoate, trifluoroacetate, 2-(2-hydroxy-1-oxopropoxy) propanoate, lactate, glycolate, pyruvate, crotonate, isovalerate cinnamate, formate, salicylate, carbamate, methylcarbamate, benzoate, gluconate, methanesulphonate, toluene, sulphonate, groups and hemiester groups of fumaric, malonic, itaconic, oxalic, maleic, succinic, tartaric, aspartic, glutamic, and malic acids.

Preferred amongst such hydrolysable deposition aids for cotton substantivity is cellulose mono acetate.

Suitable and preferred polyester-substantive deposition aids include phthalate containing polymers, more preferably a polymer having one or more nonionic hydrophilic components comprising oxyethylene, polyoxyethylene, oxypropylene or polyoxypropylene segments, and, one or more hydrophobic components comprising terephthalate segments.

Typically, oxyalkylene segments of these deposition aids will have a degree of polymerization of from 1 to about 400, although higher levels can be used, preferably from 100 to about 350, more preferably from 200 to about 300.

One type of preferred deposition aid is a copolymer having random blocks of ethylene terephthalate and polyethylene oxide terephthalate.

Another preferred polymeric deposition aid is polyester with repeat units of ethylene terephthalate units contains 10-15% by weight of ethylene terephthalate units together with 90-80% by weight of polyoxyethylene terephthalate units, derived from a polyethylene glycol of average molecular weight 0.2 kD-40 kD. Examples of this class of polymer include the commercially available material ZELCON 5126 (from DuPont) and MILEASE T (from ICI). Examples of related polymers can be found in U.S. Pat. No. 4,702,857.

Another preferred polymeric deposition aid is a sulfonated product of a substantially linear ester oligomer comprised of an oligomeric ester backbone of terephthaloyl and oxyalkyleneoxy repeat units and terminal moieties covalently attached to the backbone. These soil release agents are described fully in U.S. Pat. No. 4,968,451. Other suitable polymeric soil release agents include the terephthalate polyesters of U.S. Pat. No. 4,711,730, the anionic end-capped oligomeric esters of U.S. Pat. No. 4,721,580, and the block polyester oligomeric compounds of U.S. Pat. No. 4,702,857.

Preferred polymeric deposition aids also include the soil release agents of U.S. Pat. No. 4,877,896 which discloses anionic, especially sulfoaroyl, end-capped terephthalate esters.

Still another preferred deposition aid is an oligomer with repeat units of terephthaloyl units, sulfoisoterephthaloyl units, oxyethyleneoxy and oxy-1,2-propylene units. The repeat units form the backbone of the oligomer and are preferably terminated with modified isethionate end-caps. A particularly preferred deposition aid of this type comprises about one sulfoisophthaloyl unit, 5 terephthaloyl units, oxyethyleneoxy and oxy-1,2-propyleneoxy units in a ratio of from about 1.7 to about 1.8, and two end-cap units of sodium 2-(2-hydroxyethoxy)-ethanesulfonate. Said soil release agent also comprises from about 0.5% to about 20%, by weight of the oligomer, of a crystalline-reducing stabilizer, preferably selected from the group consisting of xylene sulfonate, cumene sulfonate, toluene sulfonate, and mixtures thereof.

The deposition aid may be straight or branched. The preferred molecular weight of the polymeric deposition aid is in the range of from about 5 kD to about 500 kD, preferably 10 kD-500 kD, more preferably 20 kD-300 kD.

Preferably, the deposition-aid polymer is present at levels such that the ratio polymer:particle solids is in the range 1:500-3:1, preferably 1:200-1:3.

Preparation Methods

The benefit agent may be present in the reaction mixture, at a level to give the benefit agent levels in the resulting particles at the levels disclosed above, although it is also possible to form "empty" particles (with or without a benefit agent carrier, for example wax) and subsequently expose them to a benefit agent which can be adsorbed into the inner region.

Deposition aids are generally added during the early part or late phase of encapsulation.

For simple core-shell particles, the core excluding benefit agent is less than or equal to 95% wt of mass, and the shell generally 5% wt or greater of the mass of the particle.

Particularly Preferred Embodiments

It is particularly preferred that the above particle comprises a fragrance contained in the core, surrounded by a shell and/or adsorbed into a carrier material, for example a mineral oil, that is surrounded by the shell and/or a poly-saccharide deposition aid exterior to the shell. Especially preferred particles have a particle size of 5-50 microns.

Use in Products

The end-product compositions of the invention may be in any physical form e.g. a solid such as a powder or granules, a tablet, a solid bar, a paste, gel or liquid, especially, an aqueous-based liquid.

The particles of the invention may be advantageously incorporated into surfactant-containing and, in particular laundry and personal care compositions. The particles are typically included in said compositions at levels of from 0.001% to 10%, preferably from 0.005% to 7.55%, most preferably from 0.01% to 5% by weight of the total composition.

For laundry applications, one active ingredient in the compositions is preferably a surface active agent or a fabric conditioning agent. More than one active ingredient may be included. For some applications a mixture of active ingredients may be used.

Formulated compositions comprising the particles of the invention may contain a surface-active compound (surfactant) which may be chosen from soap and non soap anionic, cationic, non-ionic, amphoteric and zwitterionic surface active compounds and mixtures thereof. Many suitable surface active compounds are available and are fully described in the literature, for example, in "Surface-Active Agents and Detergents", Volumes I and II, by Schwartz, Perry and Berch. The preferred surface-active compounds that can be used are soaps and synthetic non soap anionic, and non-ionic compounds.

The compositions of the invention may contain linear alkylbenzene sulphonate, particularly linear alkylbenzene sulphonates having an alkyl chain length of from C8 to C15. It is preferred if the level of linear alkylbenzene sulphonate is from 0 wt % to 30 wt %, more preferably from 1 wt % to 25 wt %, most preferably from 2 wt % to 15 wt %, by weight of the total composition.

Compositions may contain other anionic surfactants in amounts additional to the percentages quoted above. Suitable anionic surfactants are well-known to those skilled in the art. Examples include primary and secondary alkyl sulphates, particularly C8 to C15 primary alkyl sulphates; alkyl ether sulphates; olefin sulphonates; alkyl xylene sulphonates; dialkyl sulphosuccinates; and fatty acid ester sulphonates. Sodium salts are generally preferred.

Compositions may also contain non-ionic surfactant. Non-ionic surfactants that may be used include the primary and secondary alcohol ethoxylates, especially the C8 to C20 aliphatic alcohols ethoxylated with an average of from 1 to 20 moles of ethylene oxide per mole of alcohol, and more especially the C10 to C15 primary and secondary aliphatic alcohols ethoxylated with an average of from 1 to 10 moles of ethylene oxide per mole of alcohol. Non ethoxylated nonionic surfactants include alkylpolyglycosides, glycerol monoethers, and polyhydroxyamides (glucamide).

It is preferred if the level of non-ionic surfactant is from 0 wt % to 30 wt %, preferably from 1 wt % to 25 wt %, most preferably from 2 wt % to 15 wt %, by weight of a fully formulated composition comprising the particles of the invention.

Any conventional fabric conditioning agent may be used. The conditioning agents may be cationic or non-ionic. If the fabric conditioning compound is to be employed in a main wash detergent composition the compound will typically be non-ionic. For use in the rinse phase, typically they will be cationic. They may for example be used in amounts from 0.5% to 35%, preferably from 1% to 30% more preferably from 3% to 25% by weight of a fully formulated composition comprising the particles of the invention.

Suitable cationic fabric softening compounds are substantially water-insoluble quaternary ammonium materials comprising a single alkyl or alkenyl long chain having an average chain length greater than or equal to C20 or, more preferably, compounds comprising a polar head group and two alkyl or alkenyl chains having an average chain length greater than or equal to C14. Preferably the fabric softening compounds have two long chain alkyl or alkenyl chains each having an average chain length greater than or equal to C16. Most preferably at least 50% of the long chain alkyl or alkenyl groups have a chain length of C18 or above. It is preferred if the long chain alkyl or alkenyl groups of the fabric softening compound are predominantly linear.

Quaternary ammonium compounds having two long-chain aliphatic groups, for example, distearyldimethyl ammonium chloride and di(hardened tallow alkyl) dimethyl ammonium chloride, are widely used in commercially available rinse conditioner compositions. Other examples of these cationic compounds are to be found in "Surfactants Science Series" volume 34 ed. Richmond 1990, volume 37 ed. Rubingh 1991 and volume 53 eds. Cross and Singer 1994, Marcel Dekker Inc. New York".

The fabric softening compounds are preferably compounds that provide excellent softening, and are characterised by a chain melting $L\beta$ to $L\alpha$ transition temperature greater than 25 Celsius, preferably greater than 35 Celsius, most preferably greater than 45 Celsius. This $L\beta$ to $L\alpha$ transition can be measured by differential scanning calorimetry as defined in "Handbook of Lipid Bilayers", D Marsh, CRC Press, Boca Raton, Fla., 1990 (pages 137 and 337).

Substantially water-insoluble fabric softening compounds are defined as fabric softening compounds having a solubility of less than $1\times10^{-3}$ wt % in demineralised water at 20 Celsius. Preferably the fabric softening compounds have a solubility of less than $1\times10^{-4}$ wt %, more preferably from less than $1\times10^{-8}$ to $1\times10^{-6}$ wt %.

Especially preferred are cationic fabric softening compounds that are water-insoluble quaternary ammonium materials having two C12-22 alkyl or alkenyl groups connected to the molecule via at least one ester link, preferably two ester links. Di(tallowoxyloxyethyl) dimethyl ammonium chloride and/or its hardened tallow analogue is an especially preferred compound of this class.

A second preferred type comprises those derived from triethanolamine (hereinafter referred to as 'TEA quats') as described in for example U.S. Pat. No. 3,915,867. Suitable materials are, for example, N-methyl-N,N,N-triethanolamine ditallowester or di-hardened-tallowester quaternary ammonium chloride or methosulphate. Examples of commercially available TEA quats include Rewoquat WE18 and Rewoquat WE20, both partially unsaturated (ex. WITCO), Tetranyl AOT-1, fully saturated (ex. KAO) and Stepantex VP 85, fully saturated (ex. Stepan).

It is advantageous if the quaternary ammonium material is biologically biodegradable.

It is also possible to include certain mono-alkyl cationic surfactants which can be used in main-wash compositions for fabrics. Cationic surfactants that may be used include quaternary ammonium salts of the general formula $R1R2R3R4N+$ $X-$ wherein the R groups are long or short hydrocarbon chains, typically alkyl, hydroxyalkyl or ethoxylated alkyl groups, and X is a counter-ion (for example, compounds in which R1 is a C8-C22 alkyl group, preferably a C8-C10 or C12-C14 alkyl group, R2 is a methyl group, and R3 and R4, which may be the same or different, are methyl or hydroxyethyl groups); and cationic esters (for example, choline esters).

The choice of surface-active compound (surfactant), and the amount present, will depend on the intended use of the detergent composition. In fabric washing compositions, different surfactant systems may be chosen, as is well known to the skilled formulator, for hand-washing products and for products intended for use in different types of washing machine.

The total amount of surfactant present will also depend on the intended end use and may, in fully formulated products, be as high as 60 wt %, for example, in a composition for washing fabrics by hand. In compositions for machine washing of fabrics, an amount of from 5 to 40 wt % is generally appropriate. Typically compositions will comprise at least 2 wt % surfactant e.g. 2-60%, preferably 15-40% most preferably 25-35%, by weight.

Detergent compositions suitable for use in most automatic fabric washing machines generally contain anionic non-soap surfactant, or non-ionic surfactant, or combinations of the two in any suitable ratio, optionally together with soap. Compositions, when used as main wash fabric washing compositions, will generally also contain one or more detergency builders. The total amount of detergency builder in compositions will typically range from 5 to 80 wt %, preferably from 10 to 60 wt %, by weight of composition.

Inorganic builders that may be present include sodium carbonate, if desired in combination with a crystallisation seed for calcium carbonate, as disclosed in GB 1 437 950 (Unilever); crystalline and amorphous aluminosilicates, for example, zeolites as disclosed in GB 1 473 201 (Henkel), amorphous aluminosilicates as disclosed in GB 1 473 202 (Henkel) and mixed crystalline/amorphous aluminosilicates as disclosed in GB 1 470 250 (Procter & Gamble); and layered silicates as disclosed in EP 164 514B (Hoechst). Inorganic phosphate builders, for example, sodium orthophosphate, pyrophosphate and tripolyphosphate are also suitable for use with this invention.

The compositions of the invention preferably contain an alkali metal, preferably sodium, aluminosilicate builder. Sodium aluminosilicates may generally be incorporated in end product formulations amounts of from 10 to 70% by weight (anhydrous basis), preferably from 25 to 50 wt %.

The alkali metal aluminosilicate may be either crystalline or amorphous or mixtures thereof, having the general formula: 0.8 1.5 Na2O. Al2O3. 0.8 6 SiO2

These materials contain some bound water and are required to have a calcium ion exchange capacity of at least 50 mg CaO/g. The preferred sodium aluminosilicates contain 1.5 3.5 SiO2 units (in the formula above). Both the amorphous and the crystalline materials can be prepared readily by reaction between sodium silicate and sodium aluminate, as amply described in the literature. Suitable crystalline sodium aluminosilicate ion exchange detergency builders are described, for example, in GB 1 429 143 (Procter & Gamble). The preferred sodium aluminosilicates of this type are the well known commercially available zeolites A and X, and mixtures thereof.

The zeolite may be the commercially available zeolite 4A now widely used in laundry detergent powders. However, according to a preferred embodiment of the invention, the zeolite builder incorporated in the compositions of the invention is maximum aluminium zeolite P (zeolite MAP) as described and claimed in EP 384 070A (Unilever). Zeolite MAP is defined as an alkali metal aluminosilicate of the zeolite P type having a silicon to aluminium weight ratio not exceeding 1.33, preferably within the range of from 0.90 to 1.33, and more preferably within the range of from 0.90 to 1.20.

Especially preferred is zeolite MAP having a silicon to aluminium weight ratio not exceeding 1.07, more preferably about 1.00. The calcium binding capacity of zeolite MAP is generally at least 150 mg CaO per g of anhydrous material.

Organic builders that may be present include polycarboxylate polymers such as polyacrylates, acrylic/maleic copolymers, and acrylic phosphinates; monomeric polycarboxylates such as citrates, gluconates, oxydisuccinates, glycerol mono, di¬ and trisuccinates, carboxymethyloxy succinates, carboxymethyloxymalonates, dipicolinates, hydroxyethyliminodiacetates, alkyl and alkenylmalonates and succinates; and sulphonated fatty acid salts. This list is not intended to be exhaustive.

Especially preferred organic builders are citrates, suitably used in fully formulated compositions in amounts of from 5 to 30 wt %, preferably from 10 to 25 wt %; and acrylic polymers, more especially acrylic/maleic copolymers, suitably used in amounts of from 0.5 to 15 wt %, preferably from 1 to 10 wt %.

Builders, both inorganic and organic, are preferably present in alkali metal salt, especially sodium salt, form.

Compositions comprising particles according to the invention may also suitably contain a bleach system. Fabric washing compositions may desirably contain peroxy bleach compounds, for example, inorganic persalts or organic peroxyacids, capable of yielding hydrogen peroxide in aqueous solution.

Suitable peroxy bleach compounds include organic peroxides such as urea peroxide, and inorganic persalts such as the alkali metal perborates, percarbonates, perphosphates, persilicates and persulphates. Preferred inorganic persalts are sodium perborate monohydrate and tetrahydrate, and sodium percarbonate.

Especially preferred is sodium percarbonate having a protective coating against destabilisation by moisture. Sodium percarbonate having a protective coating comprising sodium metaborate and sodium silicate is disclosed in GB 2 123 044B (Kao).

The peroxy bleach compound is suitably present in a fully formulated product in an amount of from 0.1 to 35 wt %, preferably from 0.5 to 25 wt %. The peroxy bleach compound may be used in conjunction with a bleach activator (bleach precursor) to improve bleaching action at low wash temperatures. The bleach precursor is suitably present in an amount of from 0.1 to 8 wt %, preferably from 0.5 to 5 wt %.

Preferred bleach precursors are peroxycarboxylic acid precursors, more especially peracetic acid precursors and pernoanoic acid precursors. Especially preferred bleach precursors suitable for use in the present invention are N,N,N',N', tetracetyl ethylenediamine (TAED) and sodium nonanoyloxybenzene sulphonate (SNOBS). The novel quaternary ammonium and phosphonium bleach precursors disclosed in U.S. Pat. Nos. 4,751,015 and 4,818,426 (Lever Brothers Company) and EP 402 971A (Unilever), and the cationic bleach precursors disclosed in EP 284 292A and EP 303 520A (Kao) are also of interest.

The bleach system can be either supplemented with or replaced by a peroxyacid. Examples of such peracids can be found in U.S. Pat. Nos. 4,686,063 and 5,397,501 (Unilever). A preferred example is the imido peroxycarboxylic class of peracids described in EPA 325 288, EPA 349 940, DE 382 3172 and EP 325 289. A particularly preferred example is phthalimido peroxy caproic acid (PAP). Such peracids are suitably present at 0.1-12% wt, preferably 0.5-10% wt.

A bleach stabiliser (transition metal sequestrant) may also be present in fully formulated products. Suitable bleach stabilisers include ethylenediamine tetra-acetate (EDTA), the polyphosphonates such as Dequest (Trade Mark) and non phosphate stabilisers such as EDDS (ethylene diamine di succinic acid). These bleach stabilisers are also useful for stain removal especially in end-products containing low levels of bleaching species or no bleaching species.

An especially preferred bleach system comprises a peroxy bleach compound (preferably sodium percarbonate optionally together with a bleach activator), and a transition metal bleach catalyst as described and claimed in EP 458 397A, EP 458 398A and EP 509 787A (Unilever).

Advantageously in the compositions of the invention benefit agents, particularly, perfume components may be employed which are sensitive to bleaches as the encapsulation of, for example, the perfume component within the particles will provide some degree of protection to the perfume component or other benefit agent.

The fully formulated compositions may also contain one or more enzyme(s).

Suitable enzymes include the proteases, amylases, cellulases, oxidases, peroxidases and lipases usable for incorporation in detergent compositions. Preferred proteolytic enzymes (proteases) are, catalytically active protein materials which degrade or alter protein types of stains when present as in fabric stains in a hydrolysis reaction. They may be of any suitable origin, such as vegetable, animal, bacterial or yeast origin.

Proteolytic enzymes or proteases of various qualities and origins and having activity in various pH ranges of from 4-12 are available and can be used in the instant invention. Examples of suitable proteolytic enzymes are the subtilisins which are obtained from particular strains of B. *Subtilis B. licheniformis*, such as the commercially available subtilisins Maxatase (Trade Mark), as supplied by Genencor International N.V., Delft, Holland, and Alcalase (Trade Mark), as supplied by Novozymes Industri A/S, Copenhagen, Denmark.

Particularly suitable is a protease obtained from a strain of *Bacillus* having maximum activity throughout the pH range of 8-12, being commercially available, e.g. from Novozymes Industri NS under the registered trade names Esperase (Trade Mark) and Savinase (Trade Mark). The preparation of these and analogous enzymes is described in GB 1 243 785. Other commercial proteases are Kazusase (Trade Mark obtainable from Showa Denko of Japan), Optimase (Trade Mark from Miles *Kali* Chemie, Hannover, West Germany), and Superase (Trade Mark obtainable from Pfizer of U.S.A.).

Detergency enzymes are commonly employed in fully formulated products in granular form in amounts of from about 0.1 to about 3.0 wt % on product. However, any suitable physical form of enzyme may be used. Advantageously in the compositions of the invention benefit agents, for example, perfume components, may be employed which are sensitive to enzymes as the encapsulation of the perfume component (or other benefit agent) within the particles will provide some degree of protection to the perfume component (or other benefit agent).

The compositions of the invention may contain alkali metal, preferably sodium carbonate, in order to increase detergency and ease processing. Sodium carbonate may suitably be present in fully formulated products in amounts ranging from 1 to 60 wt %, preferably from 2 to 40 wt %. However, compositions containing little or no sodium carbonate are also within the scope of the invention.

The fully formulated detergent composition when diluted in the wash liquor (during a typical wash cycle) will typically give a pH of the wash liquor from 7 to 10.5 for a main wash detergent.

Particulate detergent compositions are suitably prepared by spray drying a slurry of compatible heat insensitive ingredients, and then spraying on or post-dosing those ingredients unsuitable for processing via the slurry. The skilled detergent formulator will have no difficulty in deciding which ingredients should be included in the slurry and which should not. It is particularly useful to add the perfume particles of the present invention via post-dosing.

Particulate detergent compositions preferably have a bulk density of at least 400 g/liter, more preferably at least 500 g/liter. Especially preferred compositions have bulk densities of at least 650 g/liter, more preferably at least 700 g/liter.

Such powders may be prepared either by post tower densification of spray dried powder, or by wholly non tower methods such as dry mixing and granulation; in both cases a high-speed mixer/granulator may advantageously be used. Processes using high speed mixer/granulators are disclosed, for example, in EP 340 013A, EP 367 339A, EP 390 251A and EP 420 317A (Unilever).

Liquid detergent compositions can be prepared by admixing the essential and optional ingredients thereof in any desired order to provide compositions containing components in the requisite concentrations. Liquid compositions according to the present invention can also be in compact form which means it will contain a lower level of water compared to a conventional liquid detergent.

In order that the present invention may be still further understood and carried forth into practice it will be further described with reference to the following examples:

EXAMPLES

Materials Used

Raw materials used in the following examples are summarised in Table 1.

TABLE 1

Name, supplier and description of materials used in these examples.

| Material Name | Supplier | Description/Function |
| --- | --- | --- |
| Modified Polyvinyl Alcohol (mPVOH); 15% solution | Prepared as described above | Shell forming material |
| Dextran, MWt 20K | Herochem Reagent Corp | Cross-linking agent |
| Dextran, MWt 200K | Sigma-Aldrich | Cross-linking agent |
| Sodium periodate (NaIO$_4$) | Sinopharm Chemical Reagent Corp. | Oxidant for preparing aldehyde-derived dextran |
| Octanol | Sinopharm Chemical Reagent Corp. | Solvent |
| Dodecane | Sinopharm Chemical Reagent Corp. | Solvent |
| Polyethylene glycol with Mw 600 (PEG-600) | Sinopharm Chemical Reagent Corp. | Solvent |
| Diethyl phthalate (DEP) | Damas-beta. | Solvent |
| Methyl cellulose (MC) | TCI | Polymeric agent |
| Hydroxypropyl methyl cellulose (HPMC) | Shin-Etsu Chemical Co., Ltd. | Polymeric agent |
| Hydroxypropyl cellulose (HPC) | TCI | Polymeric agent |
| Hexadecane | Aldrich | Solvent |
| Polymethylmethacrylate (PMMA) | Aldrich | Polymeric agent |
| Isopropyl myristate (IPM) | Nagase & Co., Ltd. | Solvent |
| C12-15 alkyl benzoate (CAB) | Onlystar Biotechnology Corp. | Solvent |

*The molecular weight and hydrolysis degree (saponification) of the parent PVOH are 35000 and 98%, respectively. The modification degree (MD) of butyraldehyde is 10%. WO2004/031271 describes the preparation of this modified PVOH.

Model perfumes were prepared for use in the following examples, the compositions of which are summarised in Table 2.

TABLE 2

Composition of model perfume, showing ingredient, supplier and amount.

| Ingredient | Amount (wt % of total perfume composition) | Supplier |
| --- | --- | --- |
| Perfume X | | |
| Linalool | 60% | Fluka |
| Benzyl acetate | 30% | TCl |
| Limonene | 10% | TCl |

Example 1

Preparation of Crosslinked mPVOH Capsules

The following capsules were prepared:—
Capsule 1—crosslinked with a mixture of 20 k and 200 k dextrans, in accordance with the invention.
Comparative Capsule A—crosslinked with glutaraldehyde (a commonly used crosslinking agent, known in the prior art).
Comparative Capsule B—crosslinked with 20 k dextran only.

The following method was used to prepare the capsules for use in these examples:—

An aldehyde-derived dextran was first prepared as follows:—

50 ml of a 4% aqueous solution of sodium periodate (NaIO$_4$) was prepared in a flask. The pH of the solution was adjusted to about 3.5 by adding 0.5 ml 1 M HCl and the solution was then protected from the light by covering the flask with aluminum foil. 1.5 g of dextran (MWt 20,000 or 200,000), was added to the flask and allowed to dissolve. The resultant mixture was heated to 40° C. with stirring for 3 h. The mixture was then dialyzed utilizing a dialysis tube with cut-off MWt 7000 for 48 h.

Capsule 1, comprising perfume X was then prepared using the following method:—

32 g 0.5% mPVOH solution was mixed with 480 µl of Perfume X in a single-neck flask such that a final ratio of perfume to mPVOH of 3:1 was achieved. Any further components such as polymeric agents (for example methyl cellulose), solvents (for example, isopropyl myristate)) were combined with the perfume prior to mixing with the PVOH.

The mixture was then homogenised at 6000 rpm for 2 min. 0.4 ml of aldehyde-derived dextran (dextran-CHO, CHO dosage is 0.08 mmol) (or gluteraldehyde) solution was added into the flask and the mixture was further homogenised at 6000 rpm for 3 min to form an emulsion.

The flask was subsequently placed in a water bath and heated to 50° C. at rate of about 1° C./min with gentle stirring and the mixture kept at 50° C. for 1.5 h.

500 μl of 1M HCl was then added to adjust the pH to 2-3 and the resultant mixture stirred for another 4.5 h at 50° C.

The flask was then removed and the perfume capsules, designated "Capsule 1×" had been formed the mixture.

Example 2

Particle and Dispersion Properties of Capsule 1 and Capsule A

The particle size, particle distribution and dispersion properties of the capsules were evaluated.

Particle size distribution was measured utilizing a Mastersizer 2000 (Malvern), and capsules images were observed under an optical microscope (Hirox KH7700 3D microscope).

TABLE 3

Influence of crosslinker type on capsule properties

| Capsule | Particle size (μm) | Particle size distribution | Aggregation |
|---------|--------------------|-----------------------------|-------------|
| A       | 20                 | bad                         | yes         |
| 1       | 20                 | good                        | no          |

It was found that aggregation occurred during preparation of Comparative Capsule A. Gluteraldehyde was also found to induce a rapid crosslinking reaction that was difficult to control compared to the dextran aldehydes of the present invention.

Example 3

Evaluation of Perfume Leakage from Capsules

The following method was used to evaluate perfume leakage from capsules used in these examples:— mPVOH perfume capsules (in an amount containing 15 mg perfume) were added to 2 g of Lux Body Wash, US formulation, commercially available January to February 2011, in a glass vial and the vial sealed. The mixture was then incubated at room temperature for 7 days before SPME-GC-MS evaluation for perfume leakage. 2 g Body Wash formulation containing 15 mg free perfume was prepared as the calibration standard corresponding to 100% leakage. Likewise, a logarithmic scale of target concentrations as the calibration standards were prepared corresponding to 1.0, 1.8, 3.2, 5.6, 10, 18, 32, 56% leakage.

Calibrations, samples and control were all measured ideally in the same run. The leakage of perfume capsule in Body Wash formulation was obtained by comparing the corresponding absorption peak with that of Calibrations. The details of SPME-GC-MS method are given below.

SPME-GC-MS Method:—
Equipment: Agilent 6890 GC equipped with Agilent 5975B MS and PAL CTC sampler
Incubation time: 300 s
Incubation temperature: 30° C.
Extraction time: 10 s
Desorption time: 60 s
Oven: 50° C. hold 1 min, 20° C./min to 180° C., 40° C./min to 280° C. and hold for 2 min, 80° C./min to 200° C., 60° C./min to 140° C., 40° C./min to 100° C.,
Run time: 15 min
Inlet: 250° C., splitless
Carrier: He, 1.0 ml/min
Column: DB-5MS, J&W 122-5532
Acquisition mode: SIM, m/z 71, 136, 150

Example 4

Perfume Leakage from Capsule 1 and Comparative Capsule B

Perfume leakage from Capsule 1 and Comparative Capsule B, comprising Perfume X in Body Wash formulation was measured by SPME-GC-MS as described above. The results are shown in Table 4 below. The leakage evaluation was carried out after the sample incubated at the indicated temperature and number of days.

TABLE 4

Perfume leakage from Capsule 1 and Comparative Capsule B in Body Wash formulation.

| Capsule | Dosage of crosslinker* (D20k-CHO/D200k-CHO) | Time & temp of storage | Perfume leakage** (%) | | |
|---------|---------------------------------------------|------------------------|-----------|---------|----------------|
|         |                                             |                        | Limonene  | Linalool | Benzyl acetate |
| Free perfume (control) | — | — | 100 | 100 | 100 |
| B | 0.4 ml/0 ml | 7 days 25° C. | 18 | 24 | 53 |
| 1 | 0.4 ml/0.4 ml | 20 days 25° C. | 13 | 21 | 26 |

*D20k-CHO: aldehyde-derived dextran (20k); D200k-CHO: aldehyde-derived dextran (200k); 0.2 mol/L as aldehyde concentration.
**Components of Perfume X were analysed separately.

It will be seen that, even after 20 days, leakage from the capsule in accordance with the invention is lower than from the comparative example.

The invention claimed is:

1. A particle comprising:
   (a) a core comprising a benefit agent;
   (b) a shell, wherein the shell comprises a crosslinked, hydrophobically modified polyvinyl alcohol, which comprises a crosslinking agent comprising
      i) a first dextran aldehyde having a molecular weight of from 2,000 to 50,000 Da; and
      ii) a second dextran aldehyde having a molecular weight of from greater than 50,000 to 2,000,000 Da.

2. A particle as claimed in claim 1, wherein the total amount of the first dextran aldehyde and the second dextran aldehyde is 0.5 to 5.0 wt %, by total weight of the particle.

3. A particle as claimed in claim 1 wherein the ratio of the second dextran aldehyde to the first dextran aldehyde is from 0.1 to 10, by weight.

4. A particle as claimed in claim 1 wherein the first dextran aldehyde has a molecular weight of from 5,000 to 30,000 Da; and the second dextran aldehyde has a molecular weight of from 100,000 to 500,000 Da.

5. A particle as claimed in claim 1 wherein the hydrophobically modified polyvinyl alcohol is modified with butyraldehyde.

6. A particle as claimed in claim 1 wherein the core further comprises an additional component selected from polymeric agents, solvents and mixtures thereof.

7. A particle as claimed in claim 6, wherein the solvent is selected from diethyl phthalate, isopropyl myristate, PEG-600, C12-15 alkyl benzoate and mixtures thereof.

8. A particle as claimed in claim 6, wherein the polymeric agent is selected from hydroxypropyl methyl cellulose, methyl cellulose and mixtures thereof.

9. A particle as claimed in claim 1 wherein the particle further comprises a deposition aid.

10. A particle as claimed in claim 9, wherein the deposition aid is a polysaccharide.

11. A particle as claimed in claim 1 having an average diameter of from 5 to 50 microns.

12. A particle according to claim 1 wherein the benefit agent is a perfume or antimicrobial agent.

13. A liquid composition comprising the particle as claimed in claim 1 which further comprises:
   a) surfactant selected from anionic, cationic, non-ionic, and zwitterionic; and
   b) solvent.

14. A home care or personal care composition comprising at least one particle according to claim 1 the composition selected from the group consisting of a laundry detergent, a laundry conditioner, a deodorant, an antiperspirant, a shampoo, a hair conditioner, skin care product and skin cleansing product.

15. The particle as claimed in claim 10, wherein the polysaccharide is a non-ionic polysaccharide.

* * * * *